United States Patent
Davis et al.

(10) Patent No.: US 6,788,973 B2
(45) Date of Patent: Sep. 7, 2004

(54) APPARATUS AND METHOD TO DISCRIMINATE BETWEEN TELEMETRY DOWNLINK SIGNALS AND NOISE IN AN IMPLANTED DEVICE

(75) Inventors: Timothy J. Davis, Coon Rapids, MN (US); Robert M. Ecker, Lino Lakes, MN (US); James D. Reinke, Maple Grove, MN (US); John D. Wahlstrand, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 267 days.

(21) Appl. No.: 10/117,550

(22) Filed: Apr. 2, 2002

(65) Prior Publication Data

US 2003/0187484 A1 Oct. 2, 2003

(51) Int. Cl.[7] .............................................. A61N 1/37
(52) U.S. Cl. ...................................................... 607/32
(58) Field of Search ..................................... 607/1–156

(56) References Cited

U.S. PATENT DOCUMENTS

| | | | |
|---|---|---|---|
| 4,432,360 A | 2/1984 | Mumford et al. |
| 4,437,466 A | 3/1984 | Saulson et al. |
| 4,476,868 A | 10/1984 | Thompson |
| 4,522,208 A | 6/1985 | Buffet |
| 4,531,523 A | 7/1985 | Anderson |
| 4,543,955 A | 10/1985 | Schroeppel |
| 4,545,380 A | 10/1985 | Schroeppel |
| 4,556,063 A | 12/1985 | Thompson et al. |
| 4,566,456 A | 1/1986 | Koning et al. |
| 4,590,941 A | 5/1986 | Saulson et al. |
| 4,600,017 A | 7/1986 | Schroeppel |
| 4,628,934 A | 12/1986 | Pohndorf et al. |
| 4,651,740 A | 3/1987 | Schroeppel |
| 4,676,248 A | 6/1987 | Bernston |
| 4,690,143 A | 9/1987 | Schroeppel |
| 4,708,143 A | 11/1987 | Schroeppel |
| 4,802,481 A | 2/1989 | Schroeppel |
| 4,895,152 A | 1/1990 | Callaghan et al. |
| 5,052,388 A | 10/1991 | Sivula et al. |
| 5,127,404 A | 7/1992 | Wyborny et al. |
| 5,168,871 A | 12/1992 | Grevious |
| 5,241,961 A | 9/1993 | Henry |
| 5,345,362 A | 9/1994 | Winkler |
| 5,354,319 A | 10/1994 | Wyborny et al. |
| 5,697,958 A | 12/1997 | Paul et al. |
| 6,201,993 B1 | 3/2001 | Kruse et al. |
| 6,223,083 B1 | 4/2001 | Rosar |

FOREIGN PATENT DOCUMENTS

JP       56135167 A    10/1981    ............. G01S/7/32

*Primary Examiner*—Scott M. Getzow
(74) *Attorney, Agent, or Firm*—Girma Wolde-Michael

(57) ABSTRACT

An implanted medical device (IMD) conserves power by discriminating received radio frequency (RF) signals between noise and data based on frequency. Data is processed while noise is attenuated. The IMD operates in a first, relatively low, power mode while not receiving the RF signals, in a second, higher, power mode responsive to receiving RF signals, and operates in still higher power mode when the RF signals' average frequency over a selected period is within a predetermined range. A receiver circuit receives RF signals and discriminates a data signal from noise based on average frequency of the RF signals over selected time periods. The receiver circuit operates in a power-conserving mode unless it receives RF signals, or otherwise operates in a relatively higher-power mode. The receiver transfers signals to a telemetry circuit that operates in a power-conserving mode until it receives a valid data signal to operate in higher power mode.

20 Claims, 7 Drawing Sheets

| State | Q<0:9> | Decodes | Frequency (kHz) |
|---|---|---|---|
| 0 | 00 0000 0000 | GARBAGE (possibly FAST_SLOW_CLOCKS) | 0 |
| 1 | 10 0000 0000 | GARBAGE (possibly FAST_SLOW_CLOCKS) | 12.5 |
| 2 | 11 0000 0000 | GARBAGE (possibly FAST_SLOW_CLOCKS) | 25 |
| 3 | 11 1000 0000 | GARBAGE (possibly FAST_SLOW_CLOCKS) | 37.5 |
| 4 | 11 1100 0000 | GARBAGE (possibly FAST_SLOW_CLOCKS) | 50 |
| 5 | 11 1110 0000 | GARBAGE | 62.5 |
| 6 | 11 1111 0000 | GARBAGE | 75 |
| 7 | 11 1111 1000 | GARBAGE | 87.5 |
| 8 | 11 1111 1100 | GARBAGE | 100 |
| 9 | 11 1111 1110 | GARBAGE | 112.5 |
| 10 | 11 1111 1111 | GARBAGE | 125 |
| 11 | 01 1111 1111 | FL (possibly FAST_SLOW_CLOCKS) | 137.5 |
| 12 | 00 1111 1111 | FL (possibly FAST_SLOW_CLOCKS) | 150 |
| 13 | 00 0111 1111 | FL (possibly FAST_SLOW_CLOCKS) | 162.5 |
| 14 | 00 0011 1111 | CARRIER (possibly FAST_SLOW_CLOCKS) | 175 |
| 15 | 00 0001 1111 | FH (possibly FAST_SLOW_CLOCKS) | 187.5 |
| 16 | 00 0000 1111 | FH (possibly FAST_SLOW_CLOCKS) | 200 |
| 17 | 00 0000 0111 | FH (possibly FAST_SLOW_CLOCKS) | 221.5 |
| 18 | 00 0000 0011 | GARBAGE | 225 |
| 19 | 00 0000 0001 | GARBAGE | 237.5 |

| State should be | Interval # | 20us | 20us | 20us | 20us | 20us | 20us | 20us | 20us | Decoded Output ||||
|---|---|---|---|---|---|---|---|---|---|---|---|---|---|
| | | SLAVE #1 | SLAVE #2 | SLAVE #3 || Master || SLAVE #3 | | Slave #3 | Master | Slave #1 | Slave #2 |
| FL | 1 | 200kHz | 200kHz | 150kHz | 150kHz | 150kHz | 150kHz | 200kHz | 200kHz | FL | FL | FL or CARR | FL |
| FL | 2 | 200kHz | 150kHz | 150kHz | 150kHz | 200kHz | 200kHz | 200kHz | 200kHz | FL | FL | FL | FL or CARR |
| FL | 3 | 150kHz | 150kHz | 150kHz | 200kHz | 200kHz | 200kHz | 200kHz | 200kHz | FL | FL or CARR | FL | FH or CARR |
| FH | 4 | 150kHz | 150kHz | 200kHz | 200kHz | 200kHz | 200kHz | 200kHz | 150kHz | FL or CARR | FH or CARR | FL | FH |
| FH | 5 | 150kHz | 200kHz | 200kHz | 200kHz | 200kHz | 150kHz | 150kHz | 150kHz | FH | FH | FL or CARR | FH or CARR |
| FH | 6 | 200kHz | 200kHz | 200kHz | 200kHz | 150kHz | 150kHz | 150kHz | 150kHz | FH or CARR | FH | FH or CARR | FL or CARR |
| FH | 7 | 200kHz | 200kHz | 200kHz | 150kHz | 150kHz | 150kHz | 150kHz | 150kHz | FL or CARR | FL or CARR | FH | FL |
| FL | 8 | 200kHz | 200kHz | 150kHz | 150kHz | 150kHz | 150kHz | 150kHz | 150kHz | CARR | CARR | FH or CARR | FL |
| CARR | 9 | 175kHz | 175kHz | 175kHz | 175kHz | 175kHz | 175kHz | 175kHz | 175kHz | CARR | CARR | CARR | CARR |

APPARATUS AND METHOD TO DISCRIMINATE BETWEEN TELEMETRY DOWNLINK SIGNALS AND NOISE IN AN IMPLANTED DEVICE

FIELD OF THE INVENTION

The present invention generally relates to telemetry for implantable medical devices and instruments. Specifically, the invention relates to an arrangement and a method for an implantable medical device (IMD) to distinguish between telemetry downlink signals received from a programming device and noise.

BACKGROUND OF THE INVENTION

In recent years, implantable medical device (IMD) technology has rapidly advanced. Sizes and weights of these devices have decreased, while functionality has increased. These advances have created a corresponding demand for improved two-way communication or telemetry between the IMD and an external programming device, such as an IMD programmer device. Current telemetry systems are designed to provide two-way telemetry by radio frequency (RF) signal transmission between an antenna coil located within the IMD and an antenna coil located in a programming head of the IMD programmer device. The programming head can be positioned over the patient's IMD site for programming or telemetry interrogation of the implanted device. Command instructions or data that are downloaded to the IMD are referred to as downlink transmissions, and data transmitted from the IMD to the IMD programmer device are referred to as uplink transmissions.

The IMD programmer device typically communicates with the IMD at a RF frequency of about 175 KHz. The RF carrier signal is modulated with the transmitted data using conventional modulation or encoding schemes that include, but are not limited to, pulse position modulation (PPM), frequency shift keying (FSK), differential binary phase shift keying (DBPSK) and burst counting (active and inactive states). The antenna of the IMD is typically tuned to the 175 KHz center frequency and commences generating output signals when a signal is detected at or near 175 KHz frequency. However, not all signals detected by the IMD antenna are downlink transmissions.

Preserving battery life is a primary consideration in the design of new implanted medical devices. Reducing the number of times that an IMD "wakes up" from a power saving sleep mode prevents current drain of the battery. However, the IMD sometimes "wakes up" unnecessarily because the IMD erroneously detects what appears to be an interrogation request from the programming device. The IMD at the 175 KHz frequency usually detects a normal interrogation request. Noise may be interpreted by the IMD as an interrogation request because the detected signal is near (above or below) the 175 KHz threshold frequency. After several attempts at processing the incoming signal, the IMD determines that the interrogation request is a false signal, e.g., noise.

Accordingly, there is a need for an arrangement and a method for discriminating between RF signals and noise within an implanted medical device, and that addresses the aforementioned problems, as well as other related problems.

SUMMARY OF THE INVENTION

Various embodiments of the present invention are directed to addressing the above and other needs in connection with improving frequency discrimination by a receiving circuit of an implanted medical device. More specifically, the present invention enables the IMD to prolong battery life by reducing the number of times the IMD transitions into a fully operational state after erroneously interpreting noise as a valid communication from an external IMD programmer.

According to one embodiment of the invention, a receiver circuit for an implanted medical device (IMD) discriminates between a radio frequency (RF) signal transmitting data from an external IMD programmer and noise. The IMD includes an antenna that generates output signals in response to telemetry transmissions from the IMD programmer and an analog receiver circuit that amplifies, filters, and compares the output signals to a threshold level to generate a digital signal representative of the RF signal. The receiver circuit further includes a counter circuit that receives the digital signal and counts edges of the digital signal occurring within a selected time period. The receiver circuit also includes a decoder circuit that decodes the counter value and compares the number of edges counted to a predetermined range of values before transmitting the decoded signal to a telemetry processor for further processing. The receiver circuit may also include additional counters that count the edges of the digital signal occurring over different time intervals. Each of these additional counters have an associated decoder circuit to compare the counter value to a predetermined range of values. The receiver circuit also includes an encoding circuit that receives the decoded signals from all of the decoder circuits and generates a plurality of signals for the telemetry processor of the IMD.

According to another embodiment of the invention, a method is provided for discriminating between a radio frequency (RF) signal transmitting data from an external IMD programmer and noise. The IMD includes an antenna that generates output signals in response to telemetry transmissions from the IMD programmer and an analog receiver circuit that amplifies, filters, and compares the output signals to a threshold level to generate a digital signal representative of the RF signal. The method includes counting edges of the digital signal occurring within a selected time period. The method also includes decoding the counter value and comparing the number of edges counted to a predetermined range of values before transmitting the decoded signal to a telemetry processor for further processing. The method may also include counting the edges of the digital signal over different time intervals.

The above summary of the present invention is not intended to describe each illustrated embodiment or every implementation of the present invention. The figures in the detailed description that follow more particularly exemplify these embodiments.

BRIEF DESCRIPTION OF THE DRAWINGS

The invention may be more completely understood in consideration of the following detailed description of various embodiments of the invention in connection with the accompanying drawings, in which:

FIG. 6 is a table illustrating the decodes from a gray scale decoder circuit of the frequency discrimination circuit of FIG. 5; and FIG. 7 is a table illustrating the decoded output from a frequency discrimination circuit having multiple counters that are time skewed according to an example embodiment of the invention.

Figure 1:
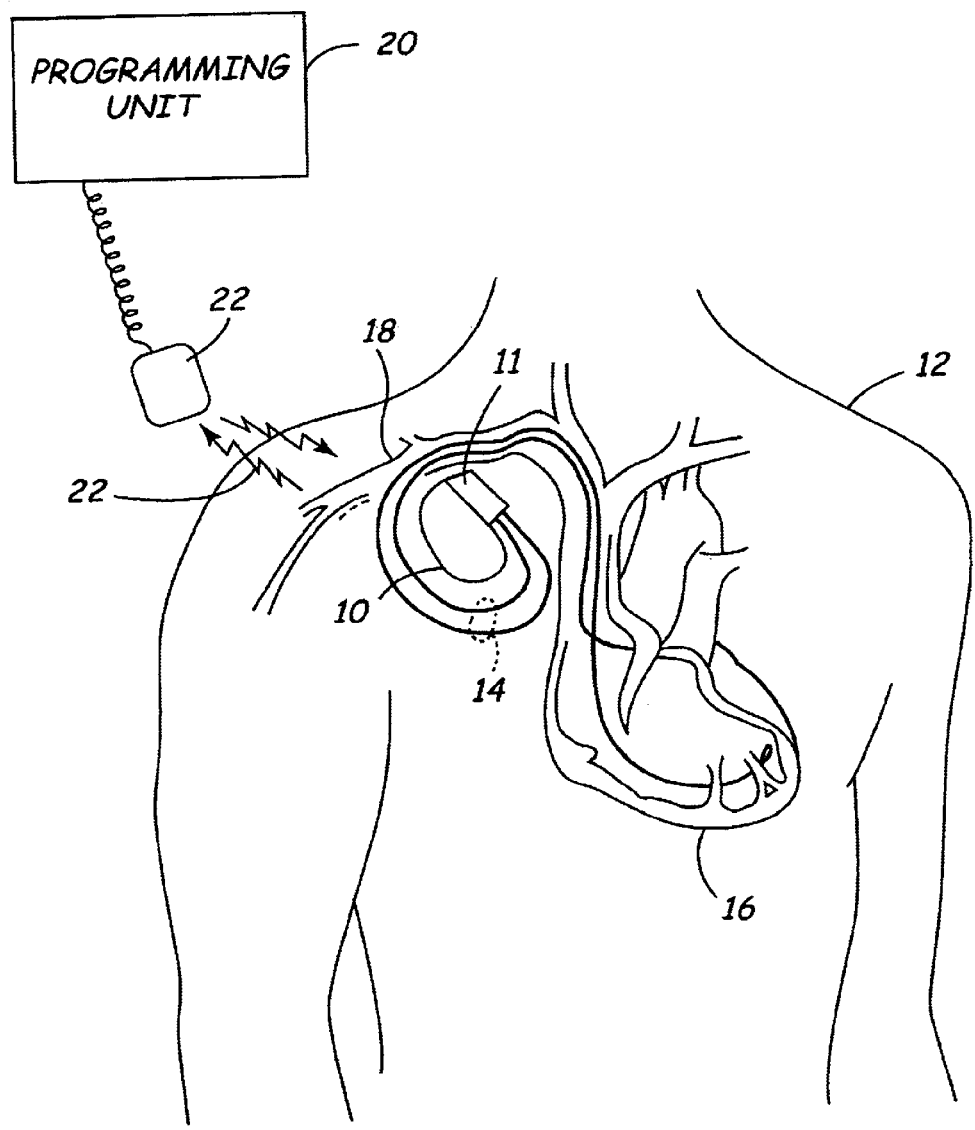
FIG. 1 is an illustration of a body-implantable device system in accordance with one embodiment of the invention, including a hermetically sealed device implanted in a patient and an external programming unit.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION

The present invention is generally directed to a receiver circuit arrangement that enables an implanted medical device (IMD) to distinguish between an RF frequency signal that is-transmitted by an external IMD programmer and noise. Improved RF frequency discrimination prolongs battery life of the IMD because noise will not be unnecessarily processed as valid signals by the IMD's receiver circuit. In addition, the receiver circuit arrangement increases the speed of transmission of data between the IMD programmer and the IMD because the IMD is not burdened with processing noise as valid signals are being received. While the present invention is not necessarily limited to such an application, the invention will be better appreciated using a discussion of example embodiments in such a specific context.

In an example embodiment, an IMD includes a telemetry processing circuit, a therapy arrangement, and a receiver circuit. The therapy arrangement is adapted to deliver a health-related therapy to a patient responsive to the telemetry processing circuit. The receiver circuit is coupled to the telemetry processing circuit and adapted to discriminate between noise and a radio frequency (RF) modulated data signal. The power mode at which the IMD operates at any given time first depends on whether the IMD is receiving an RF signal, and further depends on whether the RF signal is determined to include a valid data signal. The IMD operates in a first, very low, power mode when no RF signal is being received (assuming the therapy arrangement is not delivering the health-related therapy). Generally, only minimal circuit activity, for example a clock in the receiver circuit, draws power from an internal power supply source (e.g., a battery) when no RF signals are being received.

When RF signals are being received, whether they are noise or valid data signals being down-linked from an external programmer, additional receiver circuit components (e.g., counters, decoders, latches, encoders) function to discriminate a valid data signal from noise in the received RF signals; thereby drawing more power. However, the telemetry processing circuit and therapy arrangement remain in a relatively low-power state.

Should the receiver circuit determine that the received RF signals are noise, rather than include a valid data signal, the telemetry processing circuit and therapy arrangement remain in a relatively low-power state. However, should the receiver circuit determine that the received RF signals include a valid data signal, the valid data signal is passed on to the telemetry processing circuit which then "wakes up" to further process the valid data signal. If necessary, as determined from the valid data signal, the therapy arrangement may also "wake up" into a higher power operating state to perform any commands. The therapy arrangement reverts back to a relatively low-power state when not in use; the telemetry processing circuit reverts back to a relatively low-power state once the receiver stops passing a valid data signal; and the receiver circuit reverts back to a relatively low-power state once RF signals are no longer being received.

The received RF signals have an average frequency over a finite time period. It is expected that frequency of RF signals that include a valid data signal will be within a predetermined frequency range, 150 kHz to 200 kHz inclusive of the boundary frequencies for example, and RF signals that do not include a valid data signal (e.g., noise) will have an average frequency outside the predetermined frequency range. The receiver circuit discriminates between data and noise signals, and is further adapted to communicate the data signal to the telemetry processing circuit and attenuate noise signals having frequencies outside the predetermined frequency range.

The telemetry processing circuit operates in a power-conserving mode responsive to absence of the data signal, and operates in a relatively higher-power processing mode responsive to receiving the data signal. According to a further aspect, the receiver circuit is further adapted to identify noise having another average frequency over a portion of the first time period (e.g., the first half of the first time period, or other fixed period being a fraction of the first time period), the other average frequency not being within the predetermined frequency range during the fraction of the first time period. The receiver circuit discriminates the noise from the data signal, and blocks the noise from causing the telemetry processing circuit to operate in the relatively higher-power processing mode. Alternatively, the receiver is further adapted to identify a valid data signal over a portion of the first time period, the frequency of the valid data signal being within the predetermined frequency range during the portion of first time period.

In an example embodiment, a frequency discrimination circuit captures asynchronous downlink data at a rate of 12.5 Kbps or 1 bit every 80 $\mu$s and indicates the presence of noise in the data. The noise can be ambient or self-generated. The frequency discrimination circuit indicates to the IMD telemetry processing circuit that a downlink transmission is occurring in the presence of noise. In this example, the circuit counts the number of edges that occur within an 80 $\mu$sec time window and determines the average frequency in which the edges arrived. The frequency discrimination circuit determines whether the data that generated the edge counts is within the intended range of the frequencies. Since the data is arriving asynchronous to the frequency discrimination circuitry, multiple counters are used to measure the frequency over slightly different time intervals so that at least one counter is in synchronization with the data transitions.

FIG. 1 is an illustration of an implantable medical device system adapted for use in accordance with the present invention. The medical device system shown in FIG. 1 includes an implantable device 10—a pacemaker in this embodiment—which has been implanted in a patient 12. In accordance with conventional practice in the art, pacemaker 10 is housed within a hermetically sealed, biologically inert outer casing, which may itself be conductive so as to serve as an indifferent electrode in the pacemaker's pacing/sensing circuit. One or more pacemaker leads, collectively identified with reference numeral 14 in FIG. 1 are electrically coupled to pacemaker 10 in a conventional manner and extend into the patient's heart 16 via a vein 18. Disposed generally near the distal end of leads 14 are one or more exposed conductive electrodes for receiving electrical cardiac signals and/or for delivering electrical pacing stimuli to heart 16. As will be appreciated by those of ordinary skill in the art, leads 14 may be implanted with its distal end situated in the atrium and/or ventricle of heart 16.

Although the present invention will be described herein in one embodiment which includes a pacemaker, those of ordinary skill in the art having the benefit of the present disclosure will appreciate that the present invention may be advantageously practiced in connection with numerous other types of implantable medical device systems, and indeed in any application in which it is desirable to provide a communication link between two physically separated components, such as may occur during transtelephonic monitoring.

Also depicted in FIG. 1 is an external programming unit 20 for non-invasive communication with implanted device 10 via uplink and downlink communication channels 24, to be hereinafter described in further detail. Associated with programming unit 20 is a programming head 22, in accordance with conventional medical device programming systems, for facilitating two-way communication between implanted device 10 and programmer 20. In many known implantable device systems, a programming head such as that depicted in FIG. 1 is positioned on the patient's body over the implant site of the device, such that one or more antennae within the head can send RF signals to, and receive RF signals from, an antenna disposed within the hermetic enclosure of the implanted device or disposed within the connector block of the device, in accordance with common practice in the art.

Figure 2:
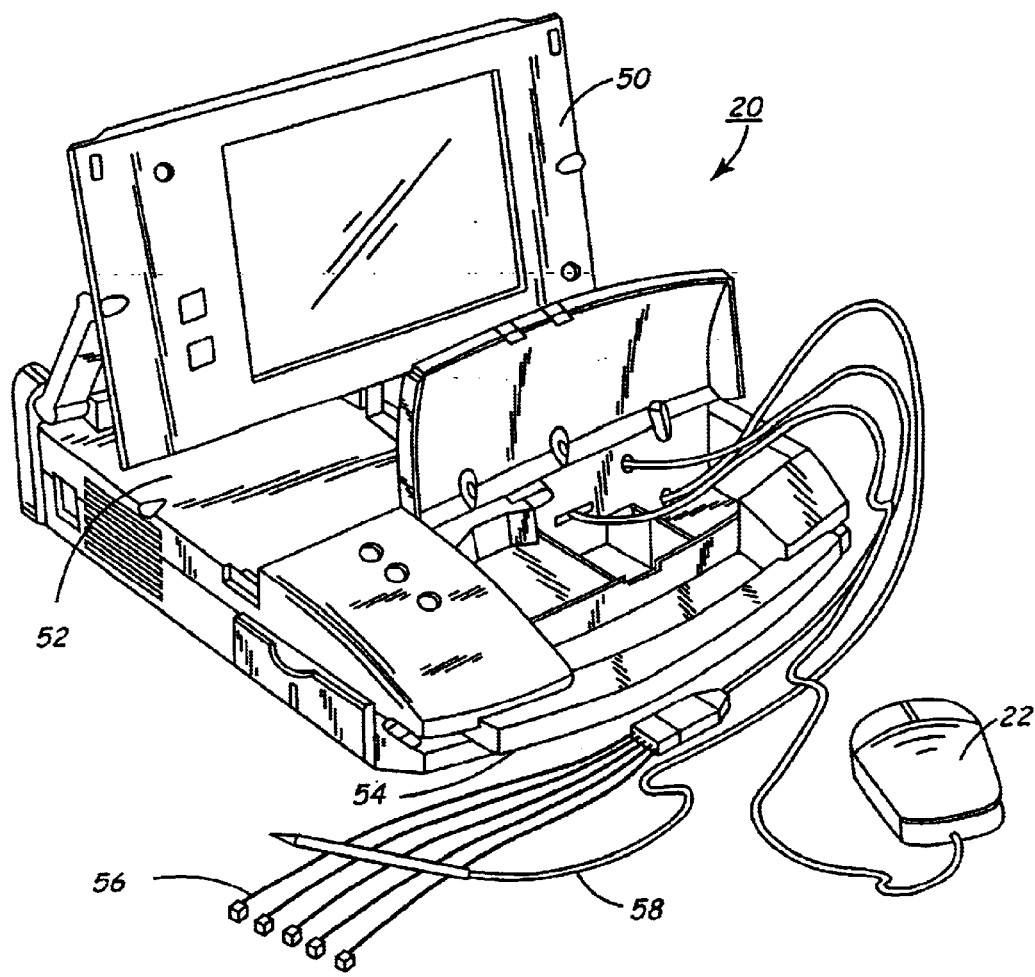
FIG. 2 is a view of the external programming unit of FIG. 1.

In FIG. 2, there is shown a perspective view of programming unit 20 in accordance with the presently disclosed invention. Internally, programmer 20 includes a processing unit (not shown in the Figures) that in accordance with the presently disclosed invention is a personal computer type motherboard, e.g., a computer motherboard including an Intel Pentium 3 microprocessor and related circuitry such as digital memory. The details of design and operation of the programmer's computer system will not be set forth in detail in the present disclosure, as it is believed that such details are well-known to those of ordinary skill in the art.

Referring to FIG. 2, programmer 20 comprises an outer housing 52, which is preferably made of thermal plastic or another suitably rugged yet relatively lightweight material. A carrying handle, designated generally as 54 in FIG. 2, is integrally formed into the front of housing 52. With handle 54, programmer 20 can be carried like a briefcase.

An articulating display screen 50 is disposed on the upper surface of housing 52. Display screen 50 folds down into a closed position (not shown) when programmer 20 is not in use, thereby reducing the size of programmer 20 and protecting the display surface of display 50 during transportation and storage thereof.

A floppy disk drive is disposed within housing 52 and is accessible via a disk insertion slot (not shown). A hard disk drive is also disposed within housing 52, and it is contemplated that a hard disk drive activity indicator, (e.g., an LED, not shown) could be provided to give a visible indication of hard disk activation.

Those with ordinary skill in the art would know that it is often desirable to provide a means for determining the status of the patient's conduction system. Normally, programmer 20 is equipped with external ECG leads 54. It is these leads which are rendered redundant by the present invention.

In accordance with the present invention, programmer 20 is equipped with an internal printer (not shown) so that a hard copy of a patient's ECG or of graphics displayed on the programmer's display screen 50 can be generated. Several types of printers, such as the AR-100 printer available from General Scanning Co., are known and commercially available.

In the perspective view of FIG. 2, programmer 20 is shown with articulating display screen 50 having been lifted up into one of a plurality of possible open positions such that the display area thereof is visible to a user situated in front of programmer 20. Articulating display screen is preferably of the LCD or electro-luminescent type, characterized by being relatively thin as compared, for example, a cathode ray tube (CRT) or the like.

Display screen 50 is operatively coupled to the computer circuitry disposed within housing 52 and is adapted to provide a visual display of graphics and/or data under control of the internal computer.

Programmer 20 described herein with reference to FIG. 2 is described in more detail in U.S. Pat. No. 5,345,362 issued to Thomas J. Winkler, entitled "Portable Computer Apparatus With Articulating Display Panel," which patent is hereby incorporated herein by reference in its entirety. The Medtronic Model 9790 programmer is the implantable device-programming unit with which the present invention may be advantageously practiced.

Figure 3:
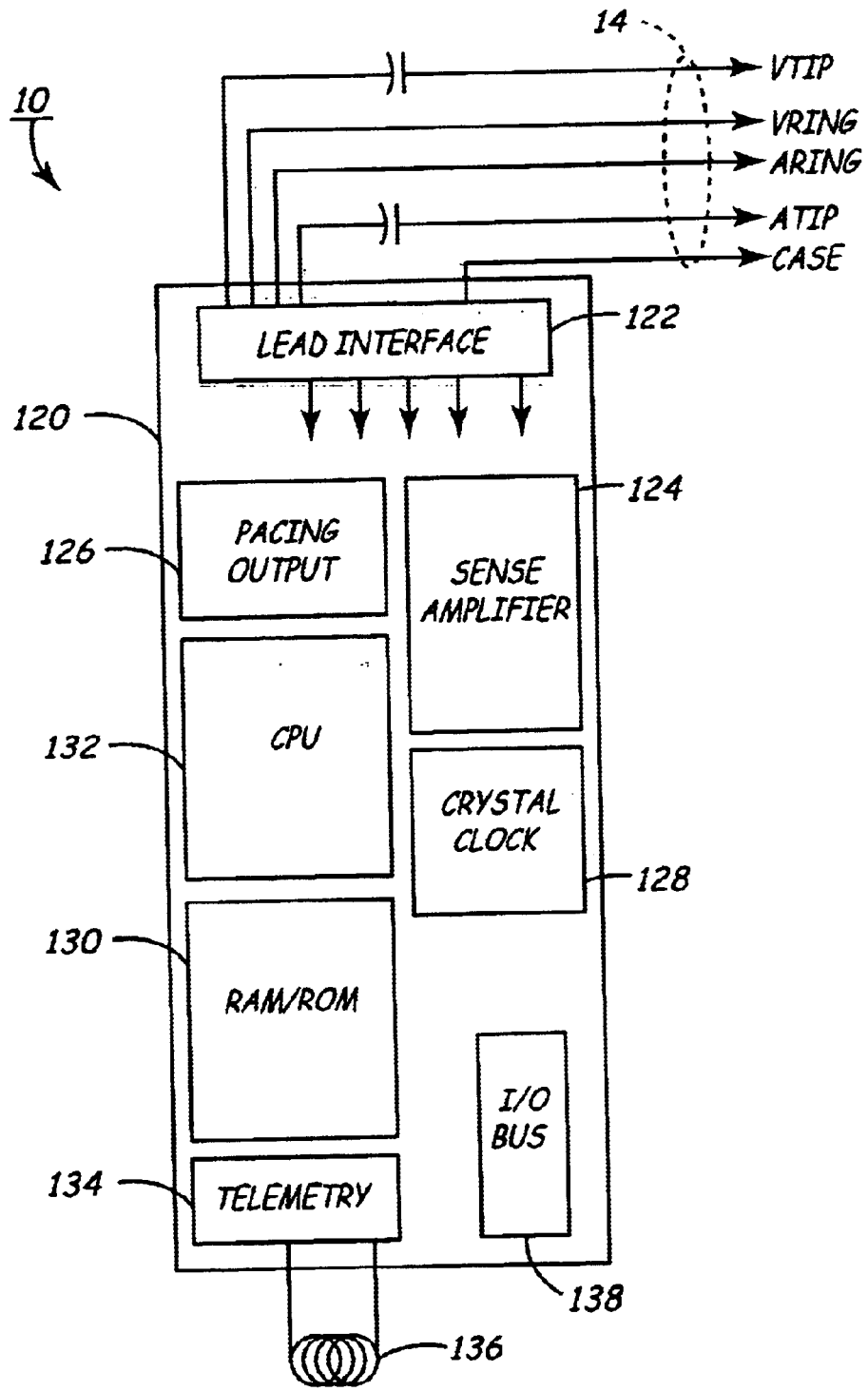
FIG. 3 is a block diagram of the body-implantable system of FIG. 1.

FIG. 3 is a block diagram of the electronic circuitry that makes up pulse generator 10 in accordance with the presently disclosed invention. As can be seen from FIG. 3, pacemaker 10 comprises a primary stimulation control circuit 120 for controlling the device's pacing and sensing functions. The circuitry associated with stimulation control circuit 120 may be of conventional design, in accordance, for example, with what is disclosed U.S. Pat. No. 5,052,388 issued to Sivula et al., "Method and apparatus for implementing activity sensing in a pulse generator." To the extent that certain components of pulse generator 10 are conventional in their design and operation, such components will not be described herein in detail, as it is believed that design and implementation of such components would be a matter of routine to those of ordinary skill in the art. For example, stimulation control circuit 120 in FIG. 3 includes sense amplifier circuitry 124, stimulating pulse output circuitry 126, a crystal clock 128, a random-access memory and read-only memory (RAM/ROM) unit 130, and a central processing unit (CPU) 132, all of which are well-known in the art.

Pacemaker 10 also includes internal communication circuit 134 so that it is capable of communicating with external programmer/control unit 20, as described in FIG. 2 in greater detail.

With continued reference to FIG. 3, pulse generator 10 is coupled to one or more leads 14 which, when implanted, extend transvenously between the implant site of pulse generator 10 and the patient's heart 16, as previously noted with reference to FIG. 1. Physically, the connections between leads 14 and the various internal components of pulse generator 10 are facilitated by means of a conventional connector block assembly 11, shown in FIG. 1. Electrically, the coupling of the conductors of leads and internal electrical components of pulse generator 10 may be facilitated by means of a lead interface circuit 122 which functions, in a multiplexer-like manner, to selectively and dynamically establish necessary connections between various conductors in leads 14, including, for example, atrial tip and ring electrode conductors ATIP and ARING and ventricular tip and ring electrode conductors VTIP and VRING, and individual electrical components of pulse generator 10, as would be familiar to those of ordinary skill in the art. For the sake of clarity, the specific connections between leads 14 and the various components of pulse generator 10 are not shown in FIG. 3, although it will be clear to those of ordinary skill in the art that, for example, leads 14 will necessarily be coupled, either directly or indirectly, to sense amplifier circuitry 124 and stimulating pulse output circuit 126, in accordance with common practice, such that cardiac electrical signals may be conveyed to sensing circuitry 124, and such that stimulating pulses may be delivered to cardiac tissue, via leads 14. Also not shown in FIG. 3 is the protection circuitry commonly included in implanted devices to protect, for example, the sensing circuitry of the device from high voltage stimulating pulses.

As previously noted, stimulation control circuit 120 includes central processing unit 132 which may be an off-the-shelf programmable microprocessor or micro controller, but in the present invention is a custom integrated circuit. Although specific connections between CPU 132 and other components of stimulation control circuit 120 are not shown in FIG. 3, it will be apparent to those of ordinary skill in the art that CPU 132 functions to control the timed operation of stimulating pulse output circuit 126 and sense amplifier circuit 124 under control of programming stored in RAM/ROM unit 130. It is believed that those of ordinary skill in the art will be familiar with such an operative arrangement.

With continued reference to FIG. 3, crystal oscillator circuit 128, in the presently preferred embodiment a 100 kHz crystal controlled oscillator, provides main timing clock signals to stimulation control circuit 120. Again, the lines over which such clocking signals are provided to the various timed components of pulse generator 10 (e.g., microprocessor 132) are omitted from FIG. 3 for the sake of clarity.

It is to be understood that the various components of pulse generator 10 depicted in FIG. 3 are powered by means of a battery (not shown) which is contained within the hermetic enclosure of pacemaker 10, in accordance with common practice in the art. For the sake of clarity in the Figures, the battery and the connections between it and the other components of pulse generator 10 are not shown.

Stimulating pulse output circuit 126, which functions to generate cardiac stimuli under control of signals issued by CPU 132, may be, for example, of the type disclosed in U.S. Pat. No. 4,476,868 to Thompson, entitled "Body Stimulator Output Circuit," which patent is hereby incorporated by reference herein in its entirety. Again, however, it is believed that those of ordinary skill in the art could select from among many various types of prior art pacing output circuits that would be suitable for the purposes of practicing the present invention.

Sense amplifier circuit 124, which is of conventional design, functions to receive electrical cardiac signals from leads 14 and to process such signals to derive event signals reflecting the occurrence of specific cardiac electrical events, including atrial contractions (P-waves) and ventricular contractions (R-waves). CPU provides these event-indicating signals to CPU 132 for use in controlling the synchronous stimulating operations of pulse generator 10 in accordance with common practice in the art. In addition, these event-indicating signals may be communicated, via uplink transmission, to external programming unit 20 for visual display to a physician or clinician.

Those of ordinary skill in the art will appreciate that pacemaker 10 may include numerous other components and subsystems, for example, activity sensors and associated circuitry. The presence or absence of such additional components in pacemaker 10, however, is not believed to be pertinent to the present invention, which relates primarily to the implementation and operation of communication subsystem 134 in pacemaker 10, and an associated communication subsystem in external unit 20.

Figure 4:
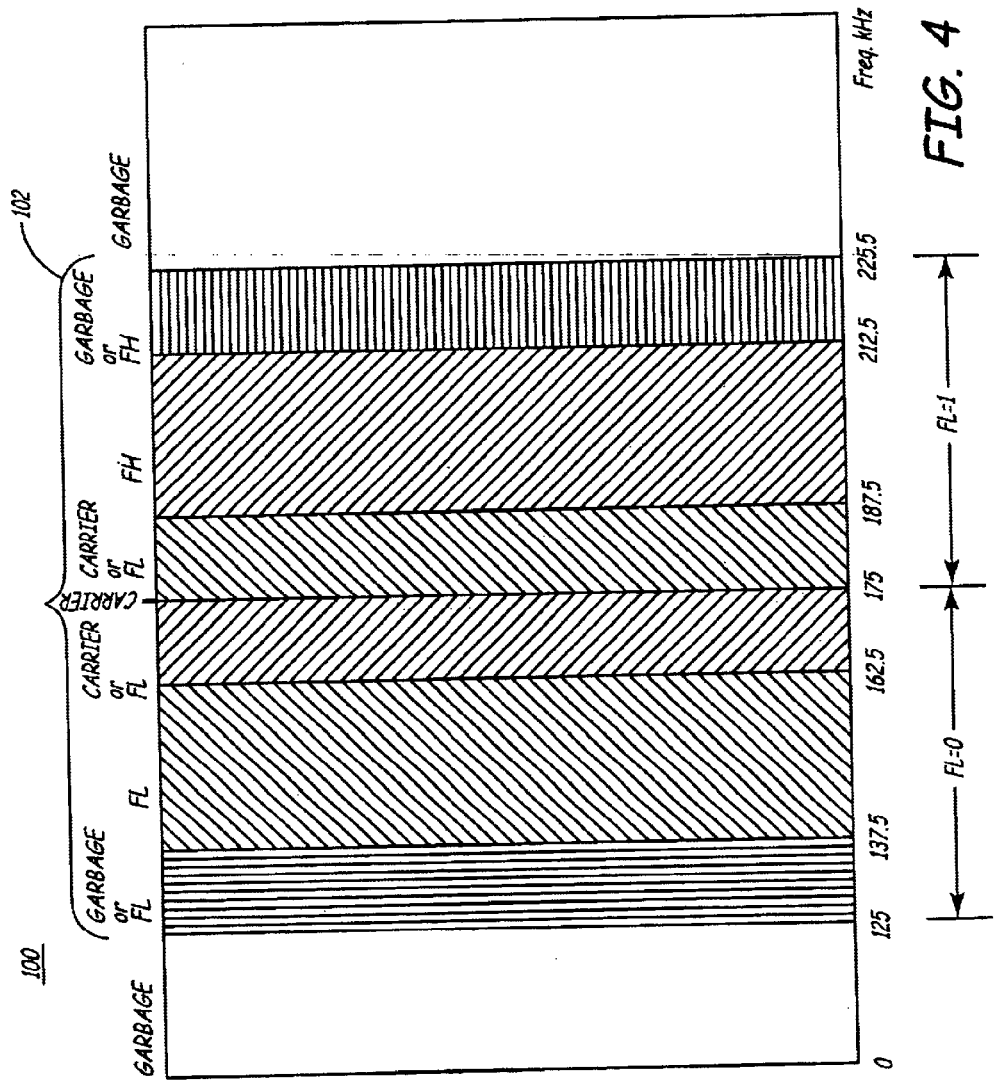
FIG. 4 is a graph that illustrates the decoded frequency ranges of a receiver circuit of an implanted medical device according to an example embodiment of the invention.

The programming head 22 depicted in FIG. 4 possesses a pair of push button switches 150 and 152 labeled INTERROGATE and PROGRAM respectively. In use, the physician places the programmer head over IMD 20 and depresses one or the other of the two buttons as shown in FIG. 4, and those depressed buttons control the overall function of the programmer circuitry of FIG. 2. Communication channel function and status to IMD 10 (not shown) is indicated via LED 54.

FIG. 4 is a graph 100 that illustrates the decoded frequency ranges of a receiver circuit of an IMD according to an example embodiment of the invention. An IMD, such as an implantable cardiac defibrillator (ICD), normally includes an antenna for telemetric communication that is tuned to a particular frequency and is electrically connected to the receiver circuit of the IMD. The antenna is tuned to a selected frequency and generates output signals in response to telemetry transmissions from the IMD programmer. The analog portion of the receiver circuit amplifies and filters the output signals from the antenna and then compares the output signals to a threshold level before transmitting the digital signal for further processing. The digital portion of the receiver circuit measures the frequency of the digital signal and determines if the frequency corresponds to a low or high frequency or noise.

In this example embodiment, the antenna is tuned to a carrier frequency of 175 KHz for radio frequency signals that are received from the external IMD programmer. The receiving circuit receives downlink signals from IMD programmer using FSK modulation. The receiver circuit interprets detected frequencies that are above 175 KHz as being FH (frequency high), where FH=1, corresponding to DATA=1. The receiver circuit interprets detected frequencies that are below 175 KHz as being FL (frequency low), where FL=1, corresponding to DATA=0.

In improving the frequency discrimination of the receiver circuit, a window 102 of acceptable frequencies is formed around the carrier frequency 175 KHz. Window 102 is divided into FL signals and FH signals. Detected signals having frequencies outside of window 102 are defined as NOISE and are not valid signals to be processed further by the receiver circuit. The outside boundary for "FH" data is 225 KHz, and the outside boundary for "FL" data is 125 KHz. Detected signals with frequencies that are less than 175 KHz, but greater than 162.5 KHz are either a CARRIER or FL. Detected signals with frequencies at 175 KHz are defined as CARRIER. Detected signals with frequencies that are less than 162.5 KHz and greater than 137.5 KHz are FL. Detected signals with frequencies that are less than 137.5 KHz and greater than 125 KHz are either NOISE or FL. Detected signals with frequencies that are greater than 175 KHz and less than 187.5 KHz are either a CARRIER or FH.

Detected signals with frequencies that are greater than 187.5 KHz and less than 212.5 KHz are FH. Detected signals with frequencies that are greater than 212.5 KHz and less than 225 KHz are either NOISE or FH.

Figure 5:
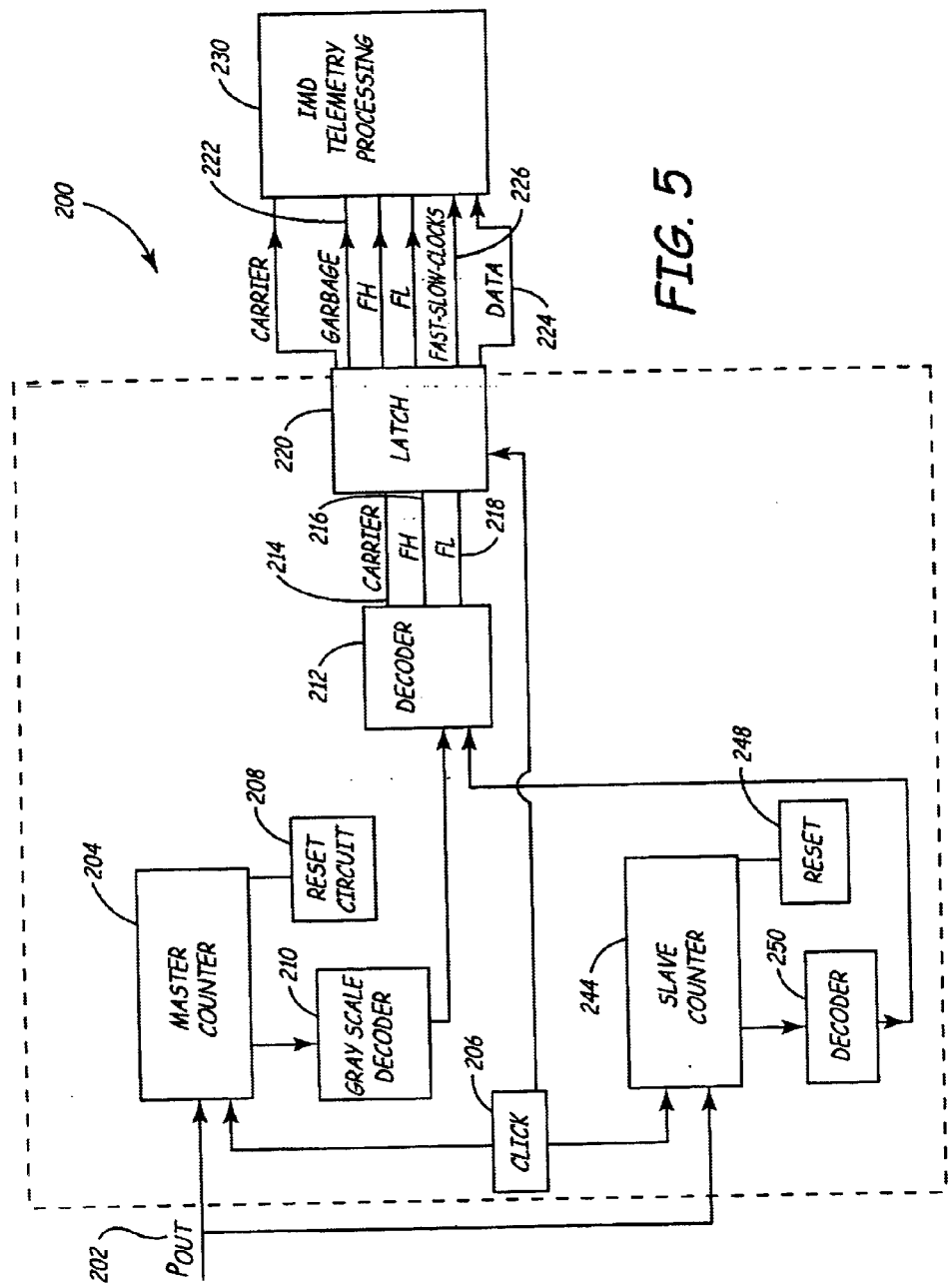
FIG. 5 is a block diagram of a frequency discrimination circuit according to an example embodiment of the invention.

FIG. 5 is a block diagram of a frequency discrimination circuit 200 according to an example embodiment of the invention. Circuit 201 is the analog part of the receiver circuit which includes the antenna, amplifier, bandpass filter, and zero crossing detector with hysteresis to generate a digital signal $P_{OUT}$ 202 representative of the frequency of the RF downlink signal. Circuit 200 is the digital part of the receiver circuit and receives the digital signal $P_{OUT}$ 202 generated by the analog part of the receiver. Circuit 230 is the telemetry processor that receives the signals generated by circuit 200 and processes the downlink data.

In this example embodiment, circuit 200 includes a system clock circuit 206, reset generator circuit 208, counter 204, counter decoder circuit 210, counter data latches 211, and data encoder 212. The system clock circuit 206 provides a periodic clock signal having a selected fixed period, for example 80 $\mu$s. Clock circuit 206 creates periodic edges (i.e., rising or falling clock transitions) defining a counting period. The data from the counter and reset the counter at latched at the end of the counting period. According to one example implementation, the counting period is 80 $\mu$s, the 80 $\mu$s period being chosen to be approximately equal to the time associated with sending a single bit of information at the 12.5 Kbps data rate. This counting duration provides the maximum number of counts and therefore, the highest resolution of the measured frequency. Those skilled in the art will recognize that clock circuit 206 can be arranged and configured to provide a clock signal having a rising edge every 80 $\mu$s, using an internal clock period of 80 $\mu$s, 40 $\mu$s, 20 $\mu$s or other sub-period.

Reset generator circuit 208 receives the clock signal from clock generator 206 and generates the reset pulse for counter 204 on the rising edge of the 80 $\mu$s clock signal. The reset generator circuit holds the counter in reset for the minimum time necessary to clear the counter. The reset generator circuit 208 also receives digital signal $P_{OUT}$ 202, and sends the signal to counter 204. Furthermore, the reset generator circuit 208 includes a means to slightly delay the signal $P_{OUT}$ if it happens to occur during a reset phase. This prevents any edges on $P_{OUT}$ from being missed by the counter, which might result in the count value being too low by 1 count. Finally, the reset generator circuit generates a clock for the counter data latches to insure the data is latched just prior to the counter being reset.

Counter circuit 204 receives the delayed $P_{OUT}$ signal and detects the number of edges occurring on the $P_{OUT}$ signal within a selected time period. Counter 204 looks at the data stream of $P_{OUT}$ signal 202 from one leading edge to another leading edge of the 80 $\mu$s clock signal. Counter 204 is a Johnson counter in one example implementation, that has a gray scale coded output resulting in only 1 of the counter outputs making a transition for each $P_{OUT}$ rising edge. This minimizes the power consumed by the counter circuit and the counter decoder circuit 210.

Counter decoder circuit 210 decodes counter 204 output signals, which are gray scale coded, and determines whether the number of edges counted is within a selected range. If the number of edges is within the predefined range, then the signal is designated as valid. If the number of edges is outside the range, then the signal is designated as NOISE, indicating that the input data clock frequency did not fall inside one of three frequency bands centered around 150 KHz, 175 KHz or 200 KHz respectively. If the $P_{OUT}$ signal is toggling at around 175 KHz, the signal is designated as the CARRIER.

Latching circuit 211 stores the digital values generated in counter decoder circuit 210, so they can only change at the rising edge of the counter circuit's respective 80 $\mu$s clock signal. This ensures that the signals are always valid, and do not change state except on the 80 $\mu$s clock signal edge.

In this example embodiment, circuit 200 further includes three other counters 244, 264, and 284, along with the associated circuits that are similar to the circuitry associated with counter 204. The present invention may be implemented using more, or fewer, than four counters (and associated circuit components). According to another example implementation, two counters are used (along with associated circuit components), each counter counting over a counting period displaced in time by one-half the counting period (e.g., the second counting period starts one-half way through the first counting period, the two counting periods being of the same duration).

Using four counters (and associated circuit components) permits decoding $P_{OUT}$ signal transitions of high frequency (FH) and low frequency (FL) that are not in-sync with all the counters. For example, a short burst of high frequency noise might occur in the $P_{OUT}$ signal at the end of one through the beginning of the next successive counting periods of a first counter, the first counter being "fooled" into determining that a signal having an average frequency within the predetermined range occurred in each of the two successive counting periods. However, the short high frequency burst of noise in the $P_{OUT}$ signal would not overlap two successive counting period of another counter having a counting period offset in time from the first counter's counting period. The other counter would count all the transitions within one counting period and determine that signal's frequency is too high to be valid data, thereby blocking passage of the signal for further processing.

Implementing the present invention with relatively more counters counting overlapping periods displaced in time allows better decoding than an implementation using relatively fewer counters, which will be more susceptible to frequency computation mistakes as illustrated above. Implementing the invention using relatively more counters produces diminishing improvement in discrimination accuracy at the expense of area, and thus IMD volume.

In another embodiment, a single counter could be used to implement the noise discrimination circuitry. The single-counter implementation measures the average frequency over an interval smaller than the time associated with a single bit of information. The multiple-counter implementation uses the maximum measurement interval possible (i.e. one bit time) to allow the highest resolution, and multiple counters ensures visibility of the data transitions on at least one of the counters. In the single counter implementation, measurements are made over ¼ the bit period to ensure visibility of data transitions. The single counter reduces circuit space requirements at the cost of reduced accuracy in measuring the average frequency.

According to another aspect of the present invention, the arrangement and configuration of a multiple counter receiver circuit allows the circuit not to miss data that occurs during a reset (a minimal duration) of any one of its counters. First, each counter has the ability to "push" the $P_{OUT}$ signal transition edge into the next counting period of the counter so that the $P_{OUT}$ signal transition edge will be counted rather than being lost. In addition, the $P_{OUT}$ signal transition edge will also be counted in overlapping counting periods of other counters. Effectively, every transition edge of the $P_{OUT}$ signal is being counted with every counter, and redundantly counted by other counters.

Clock circuit 206 clocks counters 204, 244, 264, and 284 in quadrature (i.e., delayed one-quarter counting period from one another) to ensure that at least one counter is nearly in phase with the downlink data stream. According to one example, the counting period for each counter is 80 µs; however, initiation of the counting period for counter 244 is delayed by one-quarter of a counting period (i.e., 20 µs) from the initiation of the counting period for counter 204, etc. This may be accomplished, for example, by successively clocking one of the four counter circuits on each rising edge of a clock circuit internal clock signal having a period of 20 µs. According to another example implementation, each of the four counter circuits are clocked on successive rising or falling transitions of a clock circuit internal clock signal having a period of 40 µs. Those having ordinary skill in the art will be able to implement multiple counting circuit arrangements having uniformly overlapping counting periods.

Thus, each counter receives signal $P_{OUT}$ 202 and looks at the data stream of $P_{OUT}$ simultaneously, but over a slightly different window of time. After counting the edges in their respective 80 µs windows, the counter outputs from counter 204, 244, 264, 284 are decoded by associated decoder circuits 210, 250, 270, and 290 respectively, latched by associated latching circuits 211, 251, 271, and 291 respectively, and then reset by associated reset generator circuits 208, 248, 268, and 288 respectively.

Encoding circuit 212 generates the signals SET_DATA, RESET_DATA, CARRIER, and OUT_OF_BAND from the signals FH, FL, NOISE, CARRIER, and FAST_SLOW_CLOCKS using all the outputs from all of the counter latch circuits 211, 251, 271, 291. The logic in the encoder circuit 212 looks at the number of FH, FL, CARRIER, NOISE, and FAST_SLOW_CLOCKS signals as well as the previous DATA value and makes the determination on what the next DATA value should be. In this example embodiment, the number of FH signals is compared to the number of FL signals and if there are more FH than FL signals, the SET_DATA signal is forced high and DATA is set to a "one." If there are more FL than FH signals, the RESET_DATA signal is forced high and DATA is set to a "zero." In certain situations, such as when the number of FH and FL signals are equal, it may be desirable to use the previous value of DATA to determine what the next state for DATA should be. In this example embodiment the CARRIER signals from each of the counters are counted and when all four of the counters indicate carrier is present, the CARRIER signal is set to a "one." In this example embodiment, the FAST_SLOW_CLOCKS and NOISE signals from each of the counters are examined and if any of them are set to a "one," the OUT_OF_BAND signal is set to a "one."

Data latching circuit 220 is used to prevent transitions of the DATA, CARRIER, and OUT_OF_BAND signals except at the respective clocking signal transitions (e.g., at 20 µs intervals). This prevents glitches from propagating to the telemetry processor.

If the signal is valid and is below the carrier frequency, then the signal is an FL signal indicating that the input data clock frequency is around 150 KHz and the data is "zero" ($P_{OUT}$ is toggling at a rate corresponding to a frequency that is between 137.5 KHz to 162.5 KHz). If the signal is valid and is above the carrier frequency, then the signal is an FH signal indicating that the input data clock frequency is around 200 KHz and the data is "one" ($P_{OUT}$ is toggling at a rate corresponding to a frequency that is between 187.5 KHz to 212.5 KHz). Circuit 200 generates a "one" if the input frequency of $P_{OUT}$ is in the FH range and generates a "zero" if the input frequency of $P_{OUT}$ is in the FL range. Upon reset, the DATA signal is low and the value is left at its last state until it is updated on the rising edge of the 20 µs clock signal of clock 206.

As described above, the various counters (e.g., 204, 244, 264, and 284) measure transitions occurring in the data stream of $P_{OUT}$ signal 202 during respective 80 µsec counting periods. Signal transitions of valid data are expected to be distributed fairly uniformly across the 80 µsec counting period such that approximately an equal number of transitions occur in the first 40 µsec (of each 80 µsec counting period), as occur in the last 40 µsec (of each 80 µsec counting period). Short bursts of high frequency noise in the absence of a valid data result in a group of concentrated transitions, followed by a time period having few signal transitions, or vice versa (i.e., the 80 µsec period comprises either a noise burst followed by a dead time, or a dead time followed by a noise burst). A short noise burst having a quantity of transitions that results in a "frequency" computation within frequency window 102 (e.g., transitions divided by the 80 µs period), can fool the discriminator into determining that a valid $P_{OUT}$ data signal is present, thereby causing the telemetry processing unit 230 to transition to a fully operational state (i.e., wakes up all the associated components) to process the received signals, and wasting battery life.

To prevent noise event triggering, and the resulting battery drain, the quantity of transitions is measured at some selected intermediate time period during each counting period, for example one-half way through each 80 µs window (i.e., at 40 µs). Setting the intermediate time at one half a clock period provides an existing clock signal transition (i.e., edge) used to latch the data at the intermediate time for further processing. If the first half of each 80 µs counting period includes too many, or too few transitions, a determination that valid data is present in $P_{OUT}$ is precluded. According to one example implementation, the quantity of transitions counted at an intermediate time with the clock period is compared to intermediate minimum and maximum transition count thresholds, and a signal generated whenever the actual transition count exceeds the maximum threshold, or does not exceed the minimum threshold. Counter decoder 210 and counter latch 211 also output a FAST_SLOW_CLKS signal that is an output signal indicating that the clock count during the selected intermediate time period (e.g., the first 40 µs) was either too high or too low and that a valid count of FH, FL or CARRIER cannot possibly happen within that 80 µs period. This function is duplicated in the other three counters (244, 264, 284), decoders (250, 270, 290), and latches (251, 271, 291) in such a way that their respective FAST_SLOW_CLKS signals are obtained over slightly different time windows. The FAST_SLOW_CLKS signals along with the NOISE signals from each of the counters are used in the data encoder circuit 212 to generate the OUT_OF_BAND signal which inhibits telemetry processing unit 230 from transitioning to a fully operational state (i.e., waking up all the associated components) to process the received signals, and wasting battery life.

IMD telemetry processing unit 230 receives the various signals from latch circuit 220 and processes the valid DATA signals and ignores OUT_OF_BAND signals. Telemetry processing unit 230 determines that not all of the initially "valid" signals correspond to an interrogation or programming request and that the signals received are instead noise. The present invention reduces the number of signals that telemetry processing unit 230 must fully process because signals with frequencies falling outside window 102 (e.g., 150 KHz–200 KHz) are automatically designated as OUT_OF_BAND signals. Telemetry processing unit 230 reviews signals falling within window 102 and looks for message indicators, such as wake up bursts, sync bits or flag bytes. Each time that telemetry processing unit 230 fully processes a signal, the entire signal processing system of the IMD is fully energized and the IMD consumes more battery power. Reducing the number of times that telemetry processing unit 230 transitions to a fully operational state (i.e., wakes up all the associated components) to process the received signals conserves battery life.

A more detailed discussion of receiver circuits for IMDs is provided in U.S. Pat. No. 4,676,248 to Berntson and U.S. Pat. No. 5,354,319 to Wyborny et al., which are assigned to the assignee of the present invention and are incorporated herein by reference. A more detailed discussion of a noise discrimination arrangement used in connection with an IMD is provided in U.S. Pat. No. 6,201,993 to Kruse et al., which is assigned to the assignee of the present invention and incorporated herein by reference.

FIG. 6 is a table illustrating a decoding scheme used by frequency discrimination circuit 200 of FIG. 5. In this example embodiment, counter 204 measures the frequency of $P_{OUT}$ signal 202 by counting the numbers of rising $P_{OUT}$ edges and generating ones and zeros (labeled as column 2 in the table of FIG. 6). In one example, decoder circuit 210 in state 5 (column 1) determines that the number of rising $P_{OUT}$ edges counted in 80 µs translates to a frequency of 62.5 KHz, which is a NOISE signal that will be ignored by telemetry processing circuit 230. In another example, decoder circuit 210 in state 12 determines that the number of rising $P_{OUT}$ edges counted translates to an FL (frequency low) signal having a frequency of about 150 KHz. In state 14, decoder circuit 210 determines that the number of rising $P_{OUT}$ edges counted translates to the CARRIER frequency of 175 KHz. In state 16, decoder circuit 210 determines that the number of rising $P_{OUT}$ edges counted translates to an FH (frequency high) signal having a frequency of about 200 KHz. In states 18, and 19, decoder circuit 210 determines that the number of rising $P_{OUT}$ edges counted is too high and translates to the NOISE signal having a frequency of about 225 KHz or 250 KHZ respectively. Once counter 204 reaches state 19, the counter output is held stable and will not roll over or change state until the next 80 µs counting window begins. In this example embodiment, decoder circuit 210 and counter 204 preliminarily define valid signals that telemetry processing unit 230 receives.

Including counters 244, 264, 284 improves the accuracy of distinguishing between valid message signals and noise because it insures at least one of the counters is counting the edges of $P_{OUT}$ signal 202 in synchronization with the changes in the downlink data and because it allows the measurement interval to be longer thus allowing higher accuracy of the measured frequency. Thus, including more counters in the validation circuit of a frequency discrimination circuit similar to circuit 200, which are skewed in time (e.g., one-quarter of the 80 µs counting period, or 20 µs in this example embodiment) from each other, improves frequency discrimination by increasing the accuracy of the edge count of $P_{OUT}$ signal 202.

FIG. 7 includes two examples illustrating a decoded output from frequency discrimination circuit 200 having multiple counters according to an example embodiment of the invention. Multiple counters, counting over respective periods of time offset from one another, incorporated into the validation circuit improve the validity of the decoded signals being transmitted to the telemetry processor. In this example, time skewing the additional counters improves the overall accuracy of frequency discrimination circuit 200 by ensuring that at least one of four counters is in phase with the asynchronous data. In these examples, the four counters, counter 204, counter 244, counter 264 and counter 284, receive a delayed signal $P_{OUT}$ 202 from their respective reset generator circuits, and are clocked by clock circuit 206 in quadrature (i.e., each of the respective counters counting over one of four successive overlapping periods, each successive overlapping period being delayed from the previous period by one-quarter period). Data encoder 212 receives the decoded and latched outputs of counters 204, 244, 264, and 284 and incorporates the data to recover the down-linked data signal.

In this example embodiment, each counter counts over an 80 µs period. Counter 204 begins counting the rising edges on $P_{OUT}$ 202 first, counter 244 begins counting 20 µs later, counter 264 begins counting 20 µs after counter 244 begins counting, and counter 284 begins counting 20 µs after counter 264 begins counting. Thus, each counter counts for a slightly different 80 µs window as shown in FIG. 7. FIG. 7 illustrates two examples of how the receiver circuitry operates as the frequency of $P_{OUT}$ changes back and forth between 150 KHz and 200 Khz every 80 µs. In these examples, the frequency of $P_{OUT}$ is shown over each 10 µs window. Also shown is the number of rising edges that would be counted by each counter over its 80 µs window along with the decoded state for each counter. Finally, the desired data value is shown along with the actual data value that is generated from the data encoder circuit.

In Example 1 of FIG. 7, each counter measures $P_{OUT}$ over a slightly different time interval and therefore presents results to the encoder that may be of different values based on the staggered time segment view of the incoming data. Counter 204 begins measuring 20 µs before the change in frequency of $P_{OUT}$, counter 244 begins measuring coincident with the change in frequency of $P_{OUT}$, counter 264 begins measuring 20 µs after the change in frequency of $P_{OUT}$, and counter 284 begins measuring 40 µs after the change in frequency of $P_{OUT}$. Counter 204 alternates between counts of 15 and 13, counter 244 alternates between counts of 16 and 12, counter 264 alternates between counts of 15 and 13, and counter 284 always measures a count of 14. In this example, the encoder determines the data value is a "1" whenever more counters indicate FH than FL and determines the data value is a 0 whenever more counters indicate FL than FH. In this example, the encoded data is exactly equal to the desired data, which in turn is equal to the downlink data delayed by 80 µs.

In Example 2 of FIG. 7, the downlink data has been skewed (i.e., shifted in time) 10 µs relative to Example 1. Counter 204 begins measuring 30 µs before the change in frequency of $P_{OUT}$, counter 244 begins measuring 10 µs before the change in frequency of $P_{OUT}$, counter 264 begins measuring 10 µs after the change in frequency of $P_{OUT}$, and counter 284 begins measuring 30 µs after the change in $P_{OUT}$. Counter 204 alternates between counts of 15 and 13, counter 244 alternates between counts of 16 and 12, counter 264 alternates between counts of 15, and 13, and counter 284 always reads a count of 14. In this example, the encoded data changes 10 µs prior to the desired data. In examples 1 and 2, the encoded data is equal to the downlink data, but delayed by 70 μs or 80 μs depending on how the changes in downlink data align with the 80 μs counting windows of each of the respective counters.

In another embodiment, the clock period of frequency discrimination circuit 200 is configured with a timer period other than (increased or decreased) the 80 μs period. The edge counting is adjusted accordingly to define a new range of acceptable edge counts that correspond to desired frequencies. The time skewing of the counters also varies accordingly with the change in the clock period.

In various other embodiments, the frequency discrimination circuit detects the presence of noise, which is not within window 102, and caused by a nearby noise source. In addition, high frequency oscillations normally found in noise are not mistaken for a data stream. In detecting noise, the frequency discrimination circuit can advise the IMD that the IMD is in the presence of noise and that the telemetry stream is invalid and should not be processed.

The present invention is applicable to a number of implantable medical devices that have a need to perform frequency discrimination when communicating telemetrically with an external IMD programmer. The implantable devices include, but are not limited to, to drug pumps, neurological implants, nerve stimulators, various cardiac implants and equivalent medical devices. The present invention is compatible to a number of techniques for interrogating and programming implantable medical devices.

The receiver circuit and method of the present invention improves receiver specificity, by effectively discriminating between noise and valid data. "Noise" as used herein may be of several forms, including but not limited to, RF signals that are: (1) outside the predetermined frequency band; (2) at the resonance frequency (e.g., the carrier frequency); or (3) bursting noise (e.g., a sequence of high frequency transitions followed by a dead time period, or vice-versa). The receiver circuit and method of the present invention effectively discriminates each type of noise from valid data signals as a means to conserve unnecessary IMD power usage. Conventional IMDs unnecessarily expend power in an attempt to decode noise signals into data, thereafter determining whether the data is valid. In addition, improving the specificity of the receiver reduces the likelihood that random noise could be mistaken for a down-linked message which could cause the therapy arrangement portion of the IMD to take an inappropriate action.

Furthermore, those having ordinary skill in the art will appreciate from the discussion above that the receiver circuit and method of the present invention also operate to disregard "valid" data signal contaminated by too much noise. The extra transitions due to noise imposed on noisy "valid" data signals, will appear to have an average frequency outside the predetermined frequency band, and thus not be passed on to the telemetry processing circuit. In this manner, the telemetry processing circuit need not "wake up" (and unnecessarily use power) to attempt to process noisy data signals. In other words, the telemetry processing need only "wake up" and decode valid data signals that are relatively noise-free.

The telemetry processing circuit, via clock gating, can be implemented using minimal circuitry looking for a synch character (start-of-message) in the data signal (e.g., DATA signal) since only valid data signals are passed to the telemetry processing circuit.

Various modifications, equivalent processes, as well as numerous structures to which the present invention may be applicable will be readily apparent to those of skill in the art to which the present invention is directed upon review of the present specification. The claims are intended to cover such modifications and devices.

We claim:

1. An implantable medical device (IMD) comprising:
   a telemetry processing circuit;
   a configuration control circuit coupled to the telemetry processing circuit and adapted to manage configuration parameters that define operation of the IMD; and
   a receiver circuit adapted to receive radio frequency (RF) signals, discriminate a data signal from the RF signals responsive to the frequency of the RF signals, and communicate the data signal to the telemetry processing circuit, the receiver circuit being further adapted to operate in a power-conserving mode in absence of receiving the RF signals and operate in a relatively higher-power mode responsive to receiving the RF signals,
   wherein, and the telemetry processing circuit is further adapted to operate in a power-conserving mode in absence of receiving the data signal and operate in a relatively higher-power mode responsive to receiving the data signal.

2. The IMD of claim 1, wherein the receiver circuit is further adapted to discriminate the data signal from the RF signals responsive to a first average frequency of the RF signals over a first time period and at least one other average frequency of the RF signals over at least one other time period being within a predetermined frequency range.

3. The IMD of claim 2, wherein the predetermined frequency range is between approximately 125 kHz and 225 kHz.

4. The IMD of claim 2, wherein the predetermined frequency range is between approximately 150 kHz and 200 kHz.

5. The IMD of claim 2, wherein the receiver circuit is further adapted to discriminate and attenuate noise from the RF signals responsive to either the first average frequency or the at least one other average frequency of the RF signals being outside the predetermined frequency range.

6. The IMD of claim 2, wherein the receiver circuit is further adapted to discriminate and attenuate noise from the RF signals responsive to the RF signals having an intermediate average frequency over a portion of the first period being outside the predetermined frequency range.

7. The IMD of claim 6, wherein the portion of the first time period is the first half of the first time period.

8. An implantable medical device (IMD) comprising:
   a telemetry processing circuit;
   a configuration control circuit coupled to the telemetry processing circuit and adapted to manage configuration parameters that define operation of the IMD; and
   a receiver circuit adapted to discriminate between noise and a data signal in received radio frequency (RF) signals, communicate the data signal to the telemetry processing circuit and attenuate noise,
   wherein the receiver circuit is further adapted to operate in a relatively low power mode when not receiving RF signals and operate in a relatively higher power mode when receiving RF signals, and the telemetry processing circuit is further adapted to operate in a relatively low power mode when not receiving the data signal and operate in a relatively higher power mode when receiving the data signal.

9. A receiver circuit for an implantable medical device (IMD) adapted to discriminate between noise and a radio frequency signal received from an external IMD programmer, the receiver circuit comprising:
- a converter circuit adapted to generate a digital signal from a received radio frequency signal;
- counter circuit coupled to the converter circuit and adapted to count a number of edges of the digital signal occurring within a first selected time period; and
- a decoder circuit coupled to the counter circuit adapted compare the number of edges counted with a valid range, the decoder circuit further adapted to decode the digital signal and transmit a decoded signal to a telemetry processor of the IMD responsive to comparison of the number of counted edges with the valid range.

10. A receiver circuit for an implantable medical device (IMD) adapted to discriminate between noise and a radio frequency signal received from an external IMD programmer, the receiver circuit comprising:
- a converter circuit adapted to generate a digital signal from a received radio frequency signal;
- a plurality of counter circuits coupled to the converter circuit and adapted to count respective numbers of edges of the digital signal occurring within equal time periods that are offset one from another by a selected interval;
- a plurality of decoder circuits respectively coupled to the counter circuits and adapted to compare the respective numbers of edges counted with a valid range, each decoder circuit further adapted to generate, responsive to the number of edges counted, output signals indicating whether the digital signal contains valid data and data from the digital signal; and
- a data encoder coupled to the plurality of decoder circuits, the data encoder adapted to determine whether the digital signal contains valid data responsive to the output signals from the plurality of decoder circuits and output a data signal if data is present and the data being ignored by the receiver circuit if found not be valid.

11. The receiver circuit of claim 10, wherein the output signals from the plurality of decoder circuits include a first signal indicating whether the received radio frequency signal is a carrier signal, a second signal indicating whether the received radio frequency signal is within a first frequency band, and a third signal indicating whether the received radio frequency signal is within a second frequency band, the first frequency band having a higher range of frequencies than the second frequency band.

12. The receiver circuit of claim 10, wherein the time periods are approximately 80 μsec.

13. The receiver circuit of claim 10 wherein the time periods are approximately equal to a duration of a single bit of data.

14. The receiver circuit of claim 10, wherein the plurality of counter circuits includes n counter circuits, and the time periods over which edges are counted are offset by 1/n period.

15. A method of operating an implantable medical device (IMD), in response to a radio frequency (RF) signal, the method comprising:
- operating the IMD in a first power mode while not receiving the RF signal, the first power mode being a relatively low power mode;
- operating the IMD in a second power mode responsive to receiving the RF signal, the second power mode being relatively higher than the first power mode; and
- operating the IMD in a third power mode responsive an average frequency of the RF signal over at least one selected time period being within a predetermined range, the third power mode being relatively higher than the second power mode.

16. The receiver circuit of claim 14, further comprising operating the IMD in the third power mode responsive to the average frequency RF signal in all selected time periods not being outside a predetermined average frequency range.

17. The method of claim 15, wherein the predetermined frequency range is between approximately 125 kHz and 225 kHz.

18. The method of claim 15, wherein the predetermined frequency range is between approximately 150 kHz and 200 kHz.

19. The method of claim 15, further comprising counting transitions of the RF signal within the selected time period to determine each average frequency for the selected time period, wherein all the selected time periods are of equal duration and are respectively time skewed to uniformly overlap one another.

20. The method of claim 15, further comprising operating the IMD in a forth power mode during delivery of a health-related therapy to a patient responsive to the RF signal, the fourth power mode being relatively higher than the third power mode.

* * * * *

UNITED STATES PATENT AND TRADEMARK OFFICE
CERTIFICATE OF CORRECTION

PATENT NO. : 6,788,973 B2
DATED : September 7, 2004
INVENTOR(S) : Timothy J. Davis et al.

It is certified that error appears in the above-identified patent and that said Letters Patent is hereby corrected as shown below:

<u>Column 17,</u>
Line 5, delete "counter circuit", replace with -- a counter circuit --.

Signed and Sealed this

Eleventh Day of January, 2005

JON W. DUDAS
*Director of the United States Patent and Trademark Office*